United States Patent
Augustine et al.

(10) Patent No.: US 6,420,623 B2
(45) Date of Patent: *Jul. 16, 2002

(54) BANDAGE FOR AUTOLYTIC WOUND DEBRIDEMENT

(75) Inventors: Scott D. Augustine, Bloomington; Keith J. Leland, Plymouth; John P. Rock; Donald E. Stapf, both of Minneapolis, all of MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/916,046

(22) Filed: Jul. 25, 2001

Related U.S. Application Data

(63) Continuation of application No. 09/363,568, filed on Jul. 29, 1999, now Pat. No. 6,320,093, which is a continuation of application No. 09/056,121, filed on Apr. 6, 1998, now Pat. No. 6,143,945.

(51) Int. Cl.[7] ............................................. A61F 13/00
(52) U.S. Cl. ........................ 602/41; 602/42; 602/48; 602/54; 602/56; 607/96
(58) Field of Search ............................ 602/41–59, 2; 128/888, 889; 604/307, 306, 304; 607/96, 108, 111, 112

(56) References Cited

U.S. PATENT DOCUMENTS

| | | | |
|---|---|---|---|
| 4,055,180 A | | 10/1977 | Karami ........................ 128/287 |
| 4,641,643 A | * | 2/1987 | Greer ....................... 602/54 X |
| 5,653,699 A | * | 8/1997 | Reed et al. .................. 604/307 |
| 5,817,145 A | | 10/1998 | Augustine et al. ............. 607/96 |
| 5,977,428 A | * | 11/1999 | Bozigian et al. ............... 602/48 |

FOREIGN PATENT DOCUMENTS

| | | |
|---|---|---|
| DE | 83 05 103.1 | 2/1983 |
| DE | 93 02 166.6 | 2/1993 |
| EP | 0 531 096 A2 | 3/1993 |
| EP | 0 745 365 A2 | 12/1996 |
| WO | WO 89/04158 | 5/1989 |
| WO | WO 94/00090 | 1/1994 |
| WO | WO 96/15745 | 5/1996 |

OTHER PUBLICATIONS

Translation of German Patent No. G 83 05 103.1.
Translation of German Patent No. G 93 02 166.6.
Search Report for PCT/US99/07449.

* cited by examiner

Primary Examiner—Kim M. Lewis
(74) Attorney, Agent, or Firm—Gary Cary Ware & Friedenrich

(57) ABSTRACT

A bandage for autolytic debridement includes a fluid-impermeable enclosure having a sidewall forming a margin defining an opening, and a skin-facing surface that surrounds the opening. An attachment means is disposed on the skin-facing to attach the enclosure to the skin, with the margin extending outside of and surrounding at least the bed of a wound. When the enclosure is attached to the skin it creates a closed, fluid-impermeable chamber over a wound, substantially without contacting the wound. The bandage includes a fluid absorbent material disposed in the fluid-impermeable enclosure at or near the continuous margin, and out of the opening. The fluid absorbent material is thus positioned to receive and retain exudated fluid that originates in the wound, thereby by promoting autolytic debridement. The closed, fluid-impermeable chamber maintains a near-100% humid atmosphere about the wound, thereby promoting healing of the wound. The humid atmosphere and the structure of the bandage tend to maintain the temperature of the atmosphere about the wound at or near a normothermic level in the range of about 36° C. to about 38° C., thereby maintaining physiologic processes that drive autolytic debridement and wound healing.

70 Claims, 10 Drawing Sheets

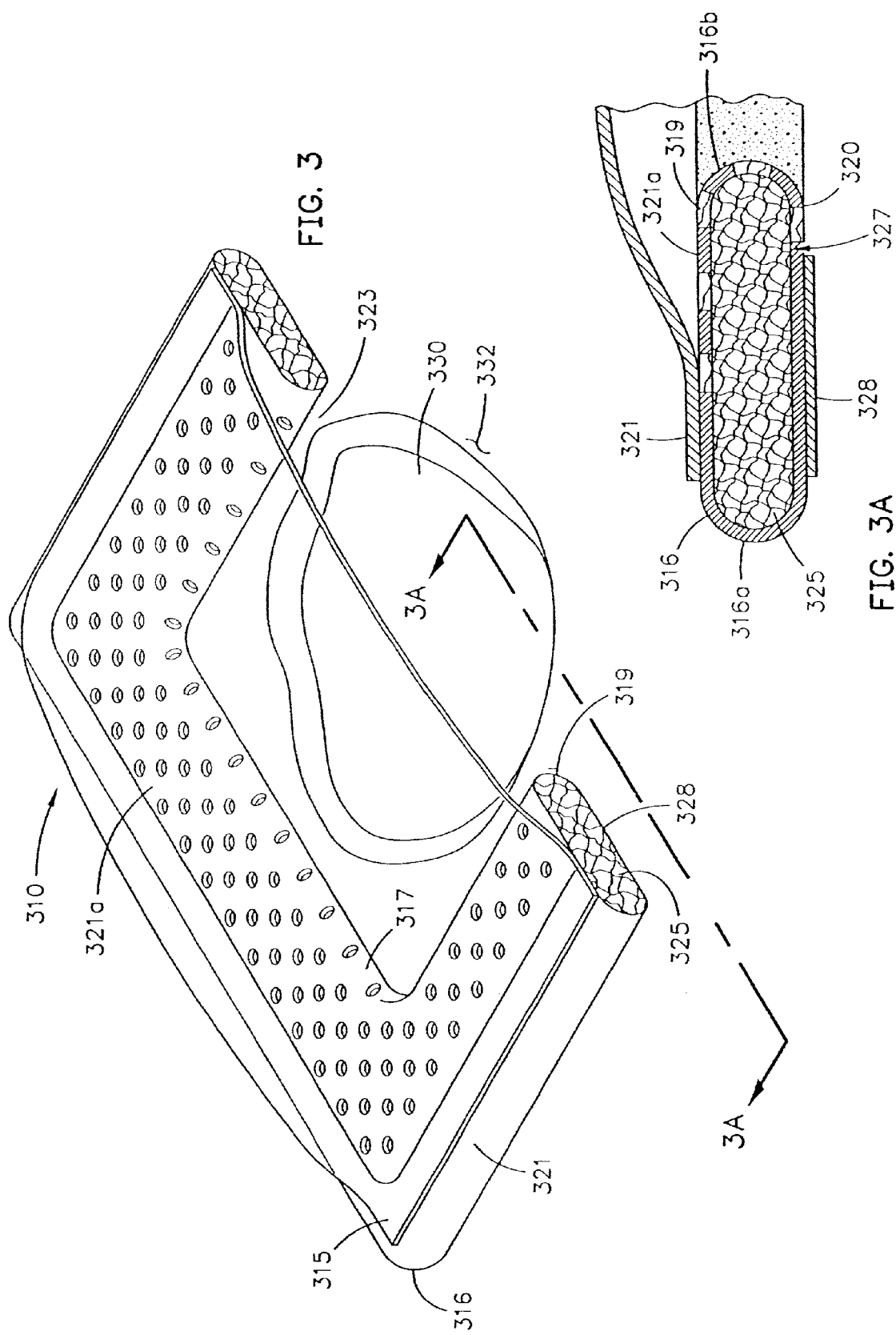

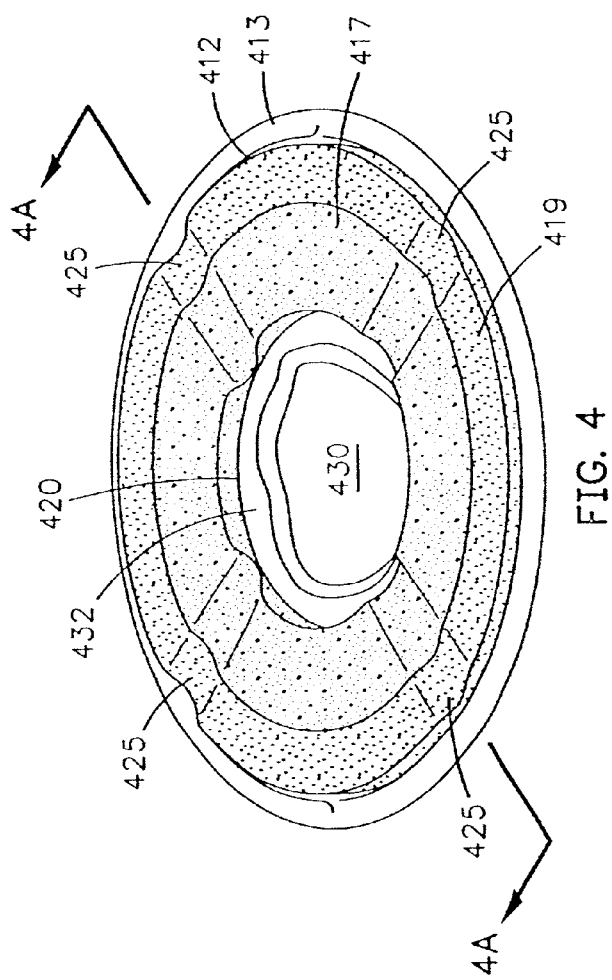
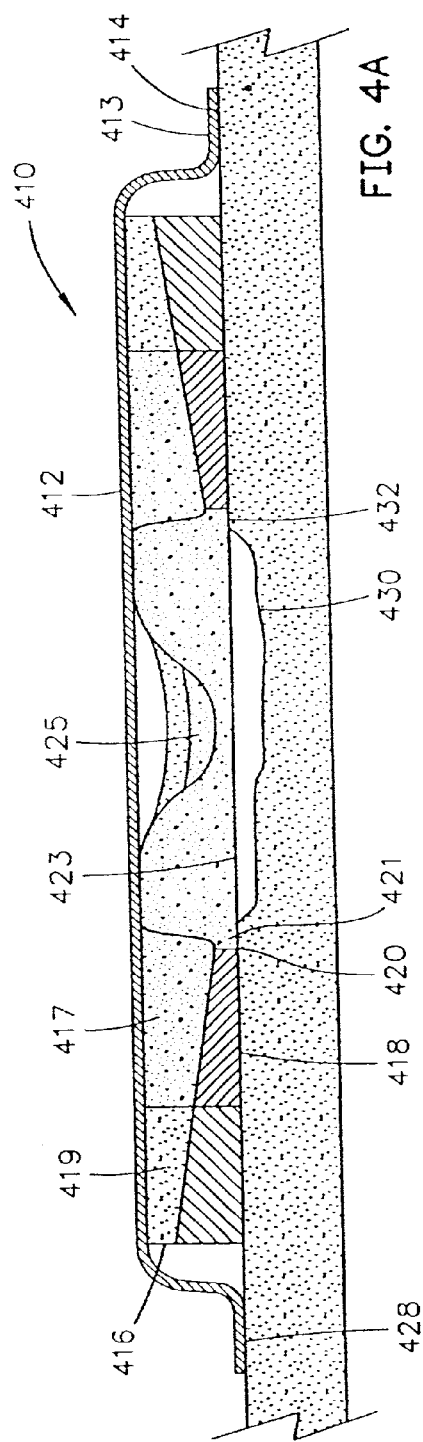

BANDAGE FOR AUTOLYTIC WOUND DEBRIDEMENT

CROSS-REFERENCES TO RELATED PATENTS AND COPENDING PATENT APPLICATIONS

This application is a continuation of patent application number 09/363,568 filed on Jul. 29, 1999, now U.S. Pat. No. 6,320,093 entitled "BANDAGE FOR AUTOLYTIC WOUND DEBRIDEMENT", which is a continuation of patent application number 09/056,121, filed Apr. 6, 1998 entitled "BANDAGE FOR AUTOLYTIC WOUND DEBRIDEMENT", now U.S. Pat. No. 6,143,945.

This application contains material related to the following commonly assigned pending U.S. patent applications:

Ser. No. 07/900,656, filed Jun. 19, 1992, for "THERMAL BODY TREATMENT APPARATUS AND METHOD";

Ser. No. 08/342,741, filed Nov. 21, 1994, for WOUND TREATMENT DEVICE";

Ser. No. 08/356,325, filed Feb. 21, 1995, for "WOUND COVERING";

Ser. No. 08/785,794, filed Jan. 21, 1997, for "NORMOTHERMIC HEATER WOUND COVERING";

Ser. No. 08/786,713, filed Jan. 21, 1997, for "NORMOTHERMIC TISSUE HEATING WOUND COVERING";

Ser. No. 08/786,714, filed Jan. 21, 1997, for "NEAR HYPOTHERMIC HEATER WOUND COVERING";

Ser. No. 08/838,618, filed Apr. 11, 1997, for "FLEXIBLE NON-CONTACT WOUND TREATMENT DEVICE";

Ser. No. 08/843,072 filed on Apr. 11, 1997 entitled "FLEXIBLE NON-CONTACT WOUND TREATMENT DEVICE WITH A SINGLE JOINT";

Ser. No. 09/056,191, filed Apr. 6, 1998 for "WOUND TREATMENT APPARATUS WITH A HEATER, A HEAT CONDUCTIVE BANDAGE, AND A HEAT-SPREADING MEANS ACTING BETWEEN THE HEATER AND BANDAGE";

Ser. No. 09055,725 filed Apr. 6, 1998 for "WOUND TREATMENT APPARATUS WITH INFRARED ABSORPTIVE WOUND COVER";

Ser. No. 09/055,597 filed Apr. 6, 1998 for "WOUND TREATMENT APPARATUS WITH A HEATER ADHESIVELY JOINED TO A BANDAGE"; and Ser. No. 09/055,605 filed Apr. 6, 1998 for "WOUND TREATMENT APPARATUS FOR NORMOTHERMIC TREATMENT OF WOUNDS".

BACKGROUND OF THE INVENTION

The invention concerns the removal of dead tissue from a wound, and more particularly. a bandage that promotes the removal of dead tissue by substances that the body itself produces.

Chronic wounds are a common aliment, afflicting over 5 million people annually in this country. The majority of chronic wounds are caused by a local or generalized vascular insufficiency that reduces blood flow to the skin and subcutaneous tissue. The most common type of chronic wounds include: pressure ulcers (decubiti, or "bed sores"); diabetic ulcers: arterial ulcers; venous ulcers; or a combination of these. Chronic wounds are full-thickness skin injuries that may be very large and that may persist for months or years.

The treatment of chronic wounds presents may challenges. First, chronic wounds frequently exude large volumes of fluid. In the case of venous leg ulcers or pressure ulcers, this fluid may primarily be a serous transudate consisting of plasma and interstitial fluid. In the case of an infected or heavily colonized wound or a wound with necrotic (dead) tissue, the fluid will contain many white blood cells, cellular debris, and toxic cellular metabolic waste products. Such fluid is commonly denominated as "exudate" or "pus".

Historically, the philosophy of wound management has encouraged drying a wound. To promote drying, a wound would be covered with a simple absorbent gauze, or left open to the air to dry. At times, heat may have been applied to the wound to enhance drying. It is now recognized that drying the wound can actually inhibit healing.

Currently, the goal of wound management is to keep a wound moist. This may be accomplished by trapping exudate or transudate in a wound bed under a substantially fluid-impermeable bandage. This practice avoids drying a wound, but leads to a new problem. In this regard, larger amounts of fluid from moderate or heavily exudating wounds may result in a pool of trapped fluid under the bandage. This pool of fluid is in constant contact with the wound and the peri-wound skin, which is a margin of skin that surrounds and abuts the wound. As a result. the wound and peri-wound tissues are constantly wet, which can lead to maceration and further damage. Additionally, the fluid contains cellular debris and metabolic waste products that may be toxic to the living tissue of the wound bed and peri-wound. The toxicity of the fluid may retard wound healing and, indeed, may damage healthy peri-wound tissue and already healed wound tissue.

Consequently, there is a need for a device that maintains an environment of high humidity over a wound in order to prevent evaporative drying of the wound while, at the same time, managing the excess fluid to keep it away from the peri-wound skin and the wound bed. In short, there is a need for a device that will keep a wound area humid, but not wet.

One significant advantage to be gained by use of such a device would be optimization of autolytic debridement. Autolytic debridement denotes the body's natural ability to break down dead tissue, thereby continuously cleaning a wound so that new skin cells can grow to fill and cover the wound, thereby promoting its healing. In this regard, "autolytic" refers to the destruction of dead tissue by agents produced by the body. "Debridement" is the removal of dead cells or tissue from a wound. Autolytic debridement is therefore the breaking down and removal of dead tissue from a wound by substances and processes that are natural to the body. This function is carried out by white blood cells generally known as phagocytes, and by a variety of enzymes. In the process the phagocytes die and add to the cellular debris of the necrotic tissue in the exudate fluid. The exudate fluid flows away from the wound, thereby removing the dead cells and other debris. Autolytic debridement under prior art wound bandages is usually ineffective at cleaning wounds because the exudate fluid collects and pools in the wound. Clinicians must frequently intervene by resorting to repeated surgical debridement in order to clean necrotic tissue from a wound. There is a need therefore to support and enhance autolytic debridement by removing exudate with its toxic waste by-products from the wound area.

Since autolytic debridement is an autogenic process, driven by the functioning of body systems, it is affected by temperature. In this regard, hypothermia is known to slow or even stop cellular functions, immune system functions, enzyme reactions, and biochemical processes. Effective phagocytosis requires an active immune system, active cellular functions, and rapid enzyme and biochemical reactions. Many wounds, because of their locations on body limbs, are hypothermic. The cool environment of these wounds slows down the process of autolytic debridement, extending the time required for healing.

Accordingly, the need for a device to keep a wound area humid, but not wet, is compounded by the need for the device to enhance autolytic debridement by carrying exudate away from the wound and keeping the wound warm.

BRIEF SUMMARY OF THE INVENTION

We have invented a device that meets these needs by maintaining a warm, humid environment at and over a wound and by collecting exudate fluid at a location away from the wound and per-wound area, thereby enabling the process of autolytic debridement.

Our invention embraces at least two components. First is a non-contact bandage with an outer shell that creates an enclosure over and about a wound, that does not touch the wound. The enclosure includes an adhesive attachment means that adhesively attaches the bandage to the skin around the wound, forming a chamber that is substantially sealed over the wound. Second, a fluid absorbent material is placed inside the chamber, away from the wound to absorb fluid from the wound.

More particularly, the invention is a bandage for autolytic debridement that includes a fluid-impermeable enclosure having a sidewall forming a margin that defines an opening, and a skin-facing surface extending beyond the margin away from the opening. An attachment means is disposed on the skin-facing surface for attaching the enclosure to skin to create a closed, fluid-impermeable chamber over a wound, substantially without contacting the wound. A fluid absorbent material is disposed in the fluid-impermeable enclosure substantially at or near the margin and out of the opening.

Significant advantages are realized when our bandage for autolytic debridement is used. In forming a closed, fluid-impermeable chamber over a wound, our bandage maintains an environment of almost 100% relative humidity over the wound, thereby preventing evaporative drying of the wound. The enclosure and its humid atmosphere tend to retain warmth or heat, thereby raising the temperature of the tissues in the peri-wound area and the wound bed to a near-normothermic level, that is a level in the range of about 36° C. to about 38° C. Dispelling hypothermia in these tissues enhances the physiologic processes that drive autolytic debridement. The collection of exudate fluid at a location away from the wound bed reduces or eliminates pooling on the wound bed and peri-wound area, which tends to accelerate autolytic debridement and promote wound healing. Finally, since the bandage does not touch the wound, its removal does not tear away growing cells at the margin and in the bed of a wound. Lifting or removal of our bandage will not cause bleeding in the wound or morbid damage to growing cells.

These advantages and other profitable characteristics of our bandage will become apparent when the following detailed description is read with reference to the below-described drawings.

BRIEF DESCRIPTION OF THE SEVERAL VIEWS OF THE DRAWING

FIG. 3 is an isometric section view of a third embodiment of a bandage for autolytic debridement. FIG. 3A is a side sectional view taken along A—A of FIG. 3.

FIG. 4 is an isometric drawing of a fourth embodiment of a bandage for autolytic debridement. FIG. 4A is a side sectional view taken along A—A of FIG. 4.

DETAILED DESCRIPTION OF THE INVENTION

Our invention is a bandage for autolytic debridement. The bandage includes a fluid-impermeable enclosure having a sidewall that forms a margin defining an opening, and a skin-facing surface surrounding the opening. An attachment means is disposed on the skin-facing surface to attach the enclosure to the skin, with the margin extending outside of and surrounding at least the bed of a wound, if not an annulus of peri-wound tissue around the wound. When the enclosure is attached to the skin it creates a closed, fluid-impermeable chamber over a wound, substantially without contacting the wound. The bandage includes a fluid absorbent material disposed in the fluid-impermeable enclosure, at or near the continuous margin, and out of the opening. The fluid absorbent material is thus positioned to receive and retain exuded fluid that originates in the wound. The closed. fluid-impermeable chamber maintains a near-100% humid atmosphere about the wound. The humid atmosphere and the structure of the bandage tend to maintain the temperature of the atmosphere about the wound at or near a normothermic level in the range of about 36° C. to about 38° C.

Reference now to the figures will provide an understanding of various embodiments of our bandage for autolytic debridement. Although a plurality of embodiments are shown, it Drill be manifest that each embodiment includes at least the above-described elements and limitations of our bandage for autolytic debridement.

Figure 1:
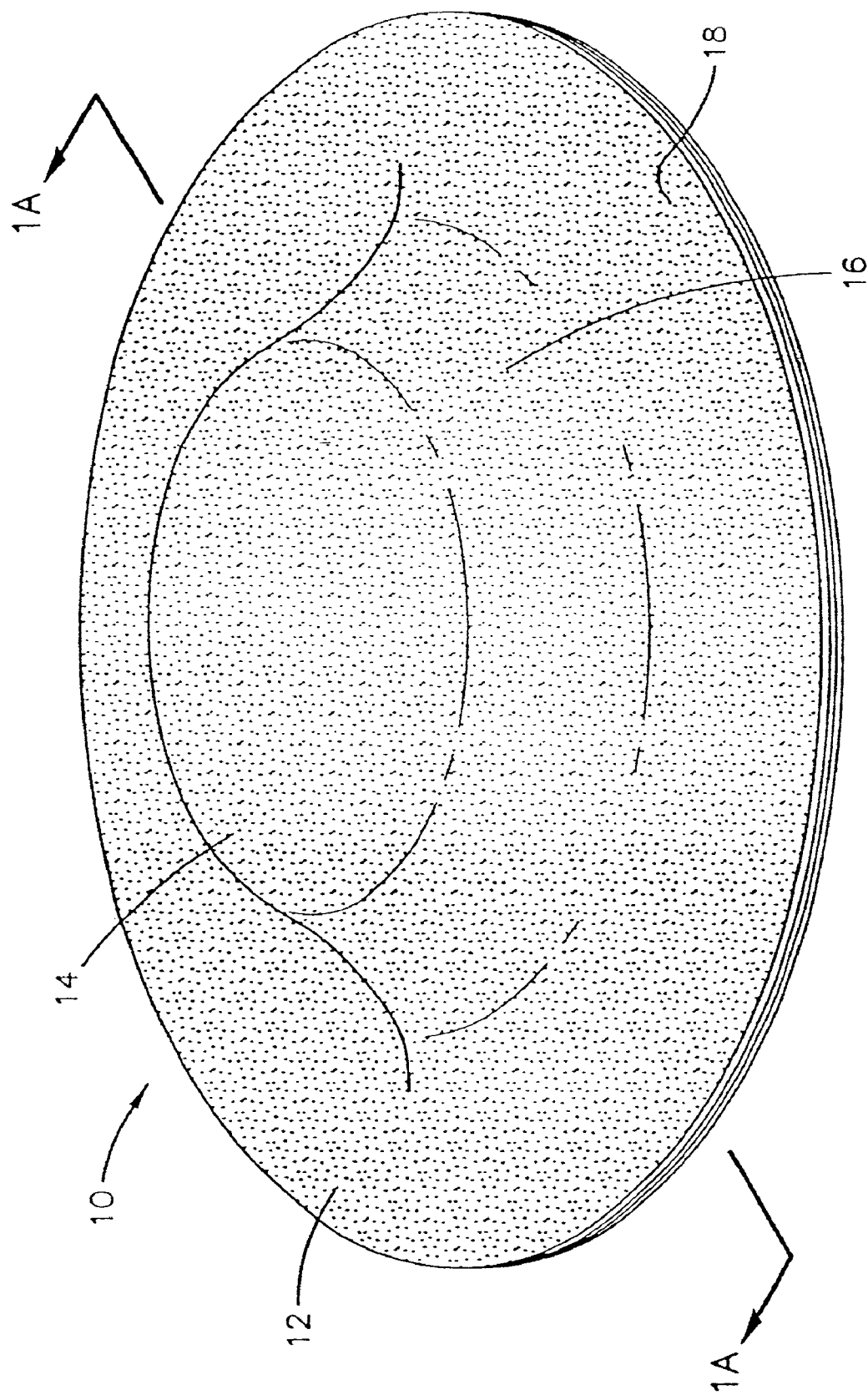
FIG. 1 is an isometric drawing of a first embodiment of a bandage for autolytic debridement.
Figure 1A:
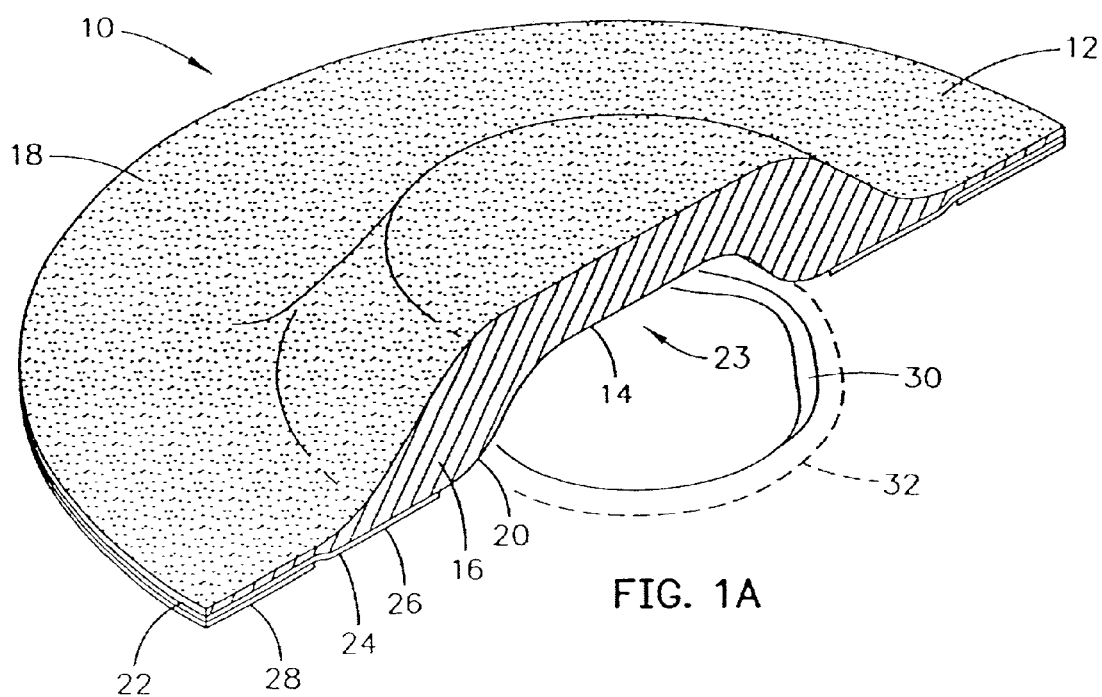
FIG. 1A is an isometric section taken along A—A in FIG. 1.
Figure 1B:
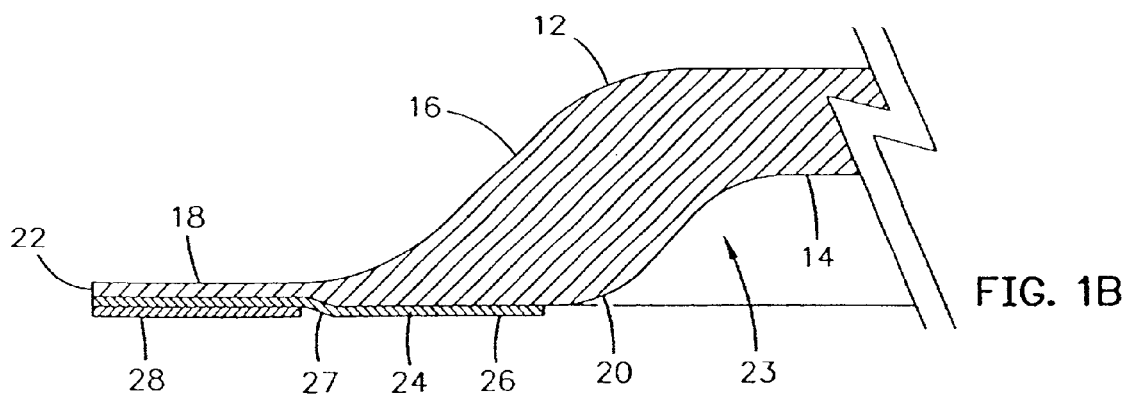
FIG. 1B is an enlarged partial side sectional view of a portion of the isometric section shown in FIG. 1A.

Referring now to FIGS. 1, 1A and 1B, a first embodiment of a bandage for autolytic debridement according to our invention is illustrated. The bandage 10 includes an enclosure 1 having the shape of an inverted saucer with a depression 14 defined by a sidewall 16 that has the shape of an annulus, preferably a continuous annulus. The sidewall 16 transitions to a compressed ring 18. The lower inside surface of the sidewall 16 defines an inner margin 20, while the outside edge of the compressed ring 18 defines an outer margin 22. The inner and outer margins are preferably, but not necessarily continuous and circular in shape. A fluid-impermeable barrier 26 having the shape of a ring extends continuously on a lower surface portion of the sidewall 16 and the compressed ring 18. The fluid-impermeable barrier 26 provides a skin-facing surface 27 of the bandage 10 on which is disposed a ring of adhesive material 28. The ring of adhesive material 28 may have a release liner on its lower surface which is stripped away when the bandage 10 is to be attached to the skin of a patient. As best seen in FIG. 1A, the bandage 10 is attached to the skin of a patient by the ring of adhesive material 28 such that the sidewall 16 and the inner margin 20 define an opening 23 that surrounds the bed of a wound 30 and a ring of peri-wound tissue 32 immediately adjacent to the wound 30. Above the opening 23, the space in the depression 14 forms a closed, dome-like structure over the wound 30 which spans the wound 30 without contacting it. The enclosure 12, the sidewall 16, and the compressed ring 18 are formed integrally. Preferably, the integral structure is formed of a material that is light, flexible, yet of a nature that provides structural integrity to the bandage 10, allowing it to stand upright when attached as shown in the figures. As an example. the bandage 10 may be formed by molding open cell foam material such as polyurethane. The material is compressed to form the compressed ring 18 only for the purpose of profiling the bandage 10. Such profiling is not a necessary element of the invention. Advantageously, the molded open cell foam material is also fluid absorbent. However the outer surface of the molded open cell foam material is treated to make it moisture impermeable. In this regard, the outer surface of the bandage 10 may be "skunned" by mechanical or heat means that are well known in the art. Alternatively, a continuous film of moisture-impermeable material may be attached or laminated to the outside surface of the bandage 10. The inside surface of the bandage 10. that is the surface of the molded open cell foam material that forms the depression 14, the lower surface of the sidewall 16, and the inner margin 20 is not treated in the manner of the outside surface of the bandage 10. In this regard, the inside surface of the bandage over, about, and surrounding the wound 30 is fluid permeable. permitting exudate from the wound 30 to pass through the inside surface of the bandage 10 into the fluid absorbent material of which the bandage 10 is formed. The barrier film layer 26 is fluid impermeable for the purpose of preventing fluid which has been absorbed by the fluid absorbent material from moistening healthy skin underneath the skin facing surface 27 and the ring of adhesive material 28. As an alternative, the entire bottom surface of the sidewall could be made fluid impermeable, in which case the barrier film layer would be eliminated and the skin-facing surface 27 would be the bottom surface of the sidewall 16. In this embodiment, the ring of adhesive material 28 would be mounted directly to the bottom surface of the sidewall 16. In operation, the ring of adhesive material 28 is prepared for attachment to the skin surface, and the bandage 10 is attached via the ring of adhesive material 28 to the skin surface, positioned so that the inner margin 20 surrounds the wound 30, set back from the peri-wound area 32. As exudate is produced in the bed of the wound 30, it flows across the peri-wound area 32, contacting the fluid absorbent material at and near the inner margin, where it is absorbed into the bandage 10. At the same time, fluid evaporates from the wound 30 and the skin, quickly raising the relative humidity within the enclosure to near 100%. The wound 30 can not dry out in a 100% humid environment. Preferably, the bandage 10 has a measurable moisture vapor transmission rate (MVTR), which is slight compared to the amount of fluid exuded from the wound 30.

The sealed enclosure formed by the bandage 10 has three purposes. First, it absorbs exudate produced at the wound 30, retaining most if not all of it in the molded open cell foam material through the inside surface of the bandage 10. This eliminates pooling of exudate in the wound and promotes autolytic debridement. This also prevents contamination and the spread of pathogens and odors. Second, the bandage 10 maintains an environment of high relative humidity over the wound 30. Finally. the sealed enclosure and its humid atmosphere effectively thermally insulate the wound and peri-wound area from the ambient environment, which tends to maintain the temperature of wound and peri-wound area in a normothermic range of from about 36° C. to about 38° C.

Figure 2:
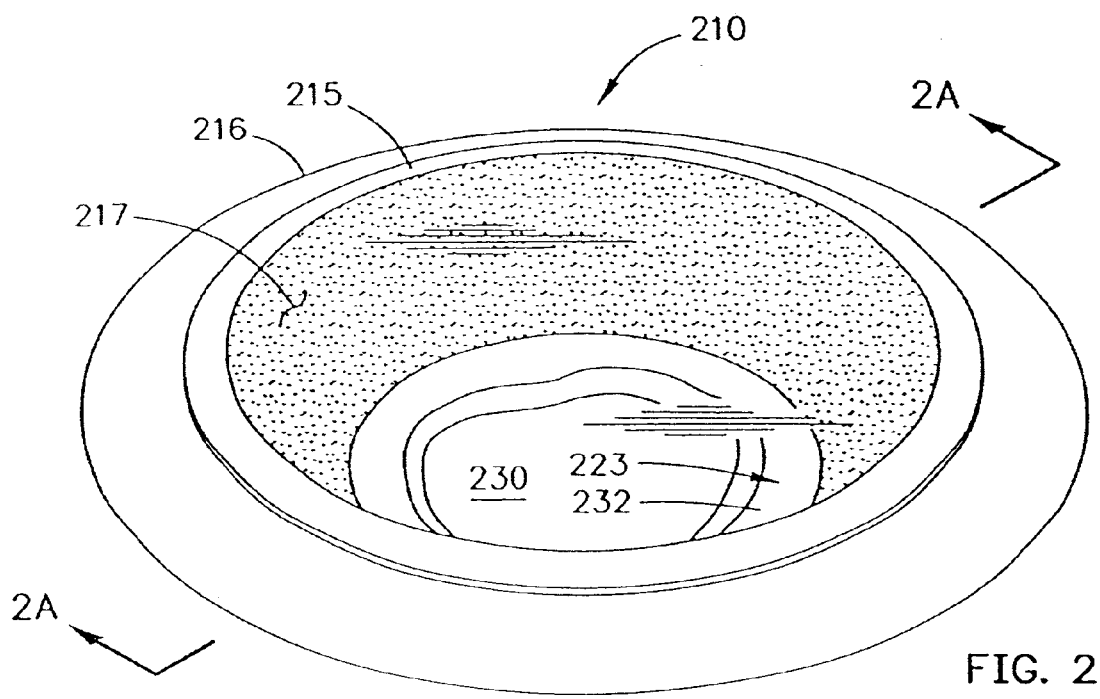
FIG. 2 is an isometric drawing of a second embodiment of a bandage for autolytic debridement.
Figure 2A:
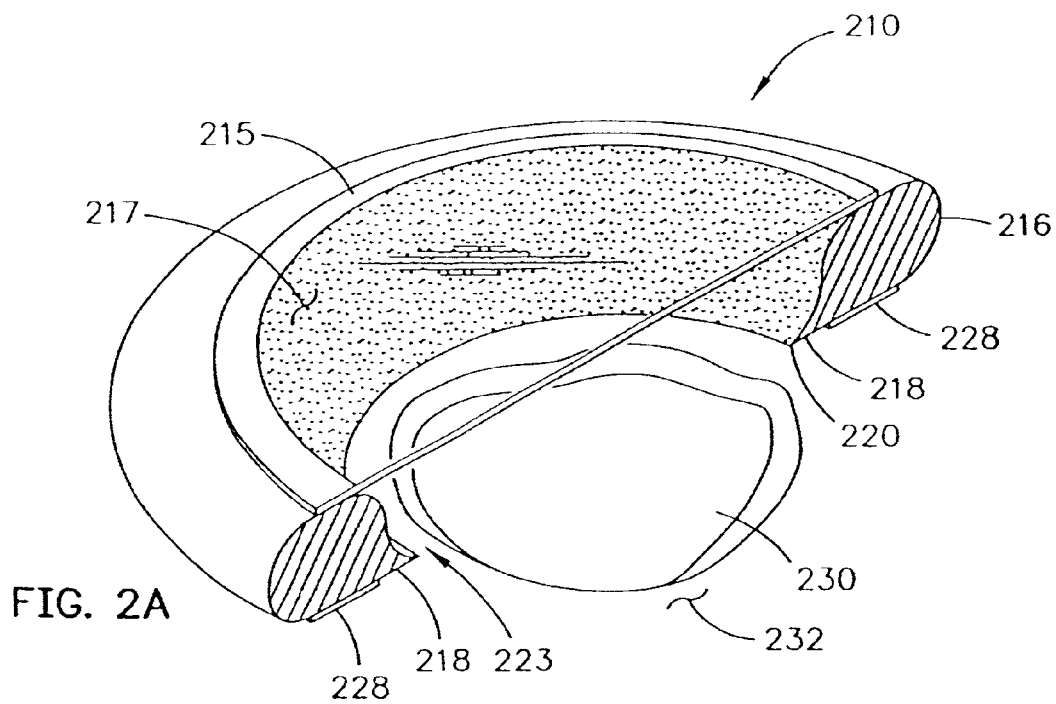
FIG. 2A is an isometric section taken alone A—A of FIG. 2.
Figure 2B:
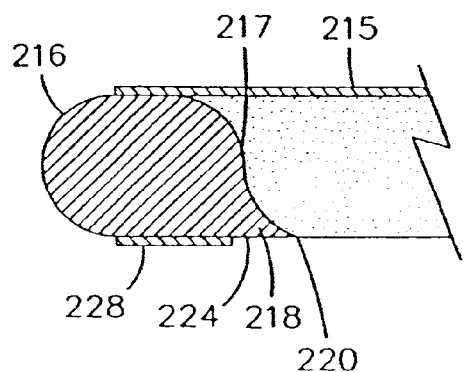
FIG. 2B is a partial side sectional view showing details of the isometric section of FIG. 2A.
Figure 2C:
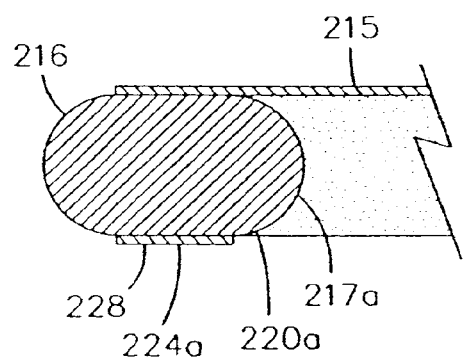
FIGS. 2C and 2D are side sectional views showing variations in the structure and elements of the second embodiment.
Figure 2D:
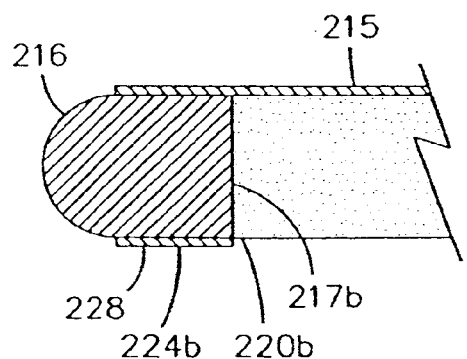

FIGS. 2 and 2A–2D illustrate a second embodiment of a bandage for autolytic debridement according to our invention. The bandage 210 includes a sidewall 216 that has the shape of an torus, preferably a continuous torus. A disk-shaped cover 215 is attached or bonded to one side of the torus, over its center. The cover 215 and sidewall 216 form an enclosure having the shape of a doughnut with a cover on one side. The sidewall 216 has an inner surface 217 that transitions to a lip 218. The lip 218 projects inwardly into the opening of the torus formed by the sidewall 216. The front edge of the lip 218 forms an inner margin 220. The inner margin is preferably, but not necessarily, continuous and circular in shape. The inner margin 220 defines an opening 223. A side surface of the torus formed by the sidewall 216 constitutes a skin-facing surface 224. A ring of adhesive material 228 is disposed on the skin-facing surface 224. The ring of adhesive material 228 may have a release liner on its lower surface which is stripped away when the bandage 210 is to be attached to the skin of the patient. As best seen in FIGS. 2A and 2B, the bandage 210 is attached to the skin of a patient by the ring of adhesive material 228 such that the sidewall 216 and the inner margin 220 define an opening 223 that surrounds the bed of a wound 230 and a ring of peri-wound tissue 232 immediately adjacent the wound 230. Above the opening 223, the space defamed by the inner wall 217 of the sidewall 216 and the cover 215 forms a closed structure over the wound 230 which spans the wound 230 without contacting it. The cover 215 and sidewall 216 are formed as separate single pieces. Preferably, the sidewall is formed of a material that is light. flexible, yet of nature that provides structural integrity to the bandage 210, allowing it to stand upright when attached as shown in the figures. As with the enclosure of the first embodiment. the sidewall 216 may be formed by molding open cell foam material such as polyurethane. The molding process forms the sidewall 216 into the shape that includes the inward facing lip 218 that transitions to the inner margin 220. As with the first embodiment. the molded open cell foam material is fluid absorbent. However, the outer surface of the molded open cell foam material is treated to make it moisture impermeable as with the first embodiment. The cover 215 may comprise a thin sheet of flexible, transparent plastic material that may be bonded by a continuous fluid-impervious seal, for example, by adhesive, to the sidewall 216 in the manner shown in the figures. For example, the cover 215 may comprise a 4 mil-thick sheet of polyethylene. The inside surface 217 of the bandage 210 is not treated in the manner of the outside surface of the bandage 210. In this regard, the inside surface 217 is fluid permeable, permitting exudate from the wound 230 to be absorbed into the fluid-absorbent material of which the bandage 210 is formed. However, the fluid-impermeable treatment of the outer surface of the sidewall 216 extends to the skin-facing surface 224, making that surface fluid-impermeable and preventing fluid which has been absorbed by the side wall 216 through the inner surface 217 from moistening healthy skin underneath the skin-facing surface 224 and the ring of adhesive 228. In operation, the ring of adhesive material 228 is prepared for attachment to the skin surface, and the bandage 210 is attached via the ring of adhesive material 228 to the skin surface, positioned so that the inner margin 220 surrounds the wound 230, set back from the peri-wound area 232. As exudate is produced in the bed of the wound 230, it flows across the peri-wound area 232, contacting the fluid absorbent material at, near, and above the inner margin 220 along the surface 217, where it is absorbed into the bandage 210. At the same time, fluid evaporates from the wound 230 and the skin, increasing the relative humidity within the enclosure formed by the cover 215 and the sidewall 216 to near 100%. This prevents the wound 230 from drying out. Preferably, the MVTR through the bandage 210 is slight compared to the amount of fluid exuded from the wound 230. The lip 218 provides contour that promotes the flow of fluid exuded from the wound 230 upward along the surface 217. Thus, if the bandage 210 is disposed so as not to be absolutely horizontal. fluid from the wound 230 will tend to flow along the upward curve of the lip 218 along the surface 217 to be absorbed through that surface into the fluid absorbent material of which the sidewall 216 is formed. In the second embodiment of our bandage for autolytic debridement, the inner margin 220 may be provided on contours other than the curved lip 218 of FIGS. 2A and 2B. For example, in FIG. 2C, the sidewall 216 may be shaped to provide an inner surface 217a that is rounded outwardly of the torus shape so that the inner margin 220a is provided where the fluid permeable inner surface 217a transitions to the fluid-impermeable skin-facing surface 224. In FIG. 2D. the sidewall 216 is shaped with a straight. flat inner surface 217b that is fluid permeable. In this case. the inner margin 220b is provided along the bottom edge of the inner surface 217b.

FIGS. 3 and 3A illustrate a third embodiment of a bandage for autolytic debridement according to our invention. The bandage 310 has a sidewall 316 in the form of a pouch having the overall shape of square or rectangular annulus. As best seen if FIG. 3A, the pouch of which the sidewall 316 is comprised has a generally rectangular cross-section with rounded ends 316a and 316b. Being a pouch, sidewall 316 has an interior space. A cover 315 is attached to an upper surface 321 of the sidewall 316, continuously around the sidewall 316 to form an enclosure therewith. The sidewall 316 has an inner side surface 317 and the surface 321 has an interior surface portion 321a. Holes 319 are provided through the inner surface portion 321a and the inner surface 317. The holes (or apertures or ports) open into the interior space of the pouch of which the sidewall 316 is comprised. An inner margin 320, which is preferably but not necessarily continuous, defines an opening 323. The interior space of the pouch of which the sidewall 316 is comprised is filled with a fluid-absorbent material 325. The bottom of the sidewall 316 has a skin-facing surface 327 that is unapertured. A square or rectangular annulus of adhesive material 328 is disposed on this skin-facing surfacing 327. The adhesive material 328 may have a release liner on its lower surface which is stripped away when the bandage 310 is to be attached to the skin of a patient. As best seen in FIG. 3, the bandage 310 is attached to the skin of a patient by the ring of adhesive 328 such that the sidewall 316 and the inner margin 320 define the opening 323, with the opening 323 surrounding the bed of a wound 330 and ring of peri-wound tissue 332. Above the opening 323, the cover 315 exhibits an upwardly rising. dome-like structure that rises above the inner surface portion 321a in order not to occlude the holes 319 in that inner surface portion. As FIG. 3 shows, the cover 315 and sidewall 316 form an enclosure over the wound 330 which spans the wound 330 without contacting it. Preferably, the cover 315 is formed of a sturdy, yet somewhat flexible, moisture-impermeable, desirably (but not necessarily) transparent material. The material should be sturdy enough to form and maintain the dome that rises over the opening 323. Flexibility is necessary to accommodate various contours that are encountered on the surface of a body. For example, the cover 315 may comprise a 4 mil-thick sheet of molded polystyrene or polyester or polyvinylchloride or equivalent material that is attached or bonded by a continuous, closed seam acting between the surface 321 of the sidewall 316 in the outer periphery of the cover 315. The bond that joins the cover 315 with the sidewall 316 may be a permanent bond, or an adhesive seam that permits the cover 315 to be removed from the sidewall 316. The sidewall 316 may be formed of the same material as the cover 315. When filled with the fluid-absorbent material 325, the sidewall 316 provides a light, flexible structure that affords structural integrity to the bandage 310, allowing it to stand upright when attached as shown in the figures. The fluid-absorbent material 325 that fills the interior of the sidewall 316 may comprise, for example, an alginate. The inside surface 317 and the inner surface portion 321a, both of which are apertured. provide ingress to fluid, permitting exudate from the wound 330 to flow into the interior space of the sidewall 316 there to be absorbed and retained by the fluid absorbent material 325. Since the surfaces 321 and 327 are unapertured, fluid that is absorbed by the fluid-absorbent material 325 is prevented from moistening healthy skin underneath the skin-facing surface 327 and the ring of adhesive 328. In operation, the ring of adhesive 328 is prepared for attachment to the skin surface, and bandage 310 is attached via the ring of adhesive 328 to the skin surface, positioned so that the inner margin 320 surrounds the wound 330, set back from the peri-wound area 332. As exudate is produced in the bed of the wound 330, it flows across the peri-wound area 332, contacting the inner surface 317 and the inner surface portion 321a, flowing through the apertures 319 into the interior of the sidewall 316 where it is absorbed by the fluid absorbent material 325. At the same time, fluid evaporates from the wound 330 and the skin, raising the relative humidity within the enclosure to near 100%, thereby preventing drying of the wound 330. Preferably, the material of which the cover 315 and sidewall 316 are formed provides a measurable MVTR, which is slight compared to the amount of fluid exuded from the wound 330.

Referring now to FIGS. 4 and 4A, a fourth embodiment of the bandage for autolytic debridement according to our invention is illustrated. The bandage 410 includes a cover 412 that is circularly shaped and molded to form an enclosure with a flattened dome. At its margin, the cover 412 transitions to a lip 413, on the bottom of which is a first skin-facing surface 414. A sidewall 416 has the shape of an annulus, preferably a continuous annulus that includes an inner ring of material 417 and an outer ring of material 419. The bottom surface of the inner ring of material 417 is a second skin facing surface 418. An inner margin 420 defines an inner circumference of the inner ring of material 417. An inner surface 421 rises from the inner margin 420. The sidewall 416 and the inner margin 420 define an opening 423. One or more grooves 425 extend radially on the upper surface of the sidewall 416 extending from the top of the inner surface 421 to the outer periphery of the sidewall 416, traversing both the inner and outer rings of material 417 and 419. A ring of adhesive material 428 is disposed on the first skin-facing surface 414. The ring of adhesive material 428 may have a release liner on its lower surface which is stripped away when the bandage 410 is to be attached to the skin of the patient. As seen in the figures, the bandage 410 is attached to the skin of a patient by the ring of adhesive material 428 such that the opening 423 defined by the sidewall 416 and the inner margin 420 surrounds the bed of a wound 430 and a ring of peri-wound tissue 432 immediately adjacent to the wound 430. Above the opening 423, a closed space is defined over the wound 430 by the sidewall 416 and the cover 412. The cover 412 and sidewall 416 may be formed as separate single pieces. Preferably, the sidewall is formed of two materials, both light, flexible, yet of a nature that provides structural integrity to support the cover 412 upright over the wound 430 when attached as shown in the figures. The sidewall 416 is preferably a single integral piece that unifies the inner ring of material 417 and the outer ring of material 419. The inner ring of material 417 is, preferably, a fluid absorbent material such as a molded open cell foam. Preferably the second skin-facing surface 418 is treated so as to be fluid impermeable. However the inner surface 421 and the upper surface of the inner ring of material 417 are fluid permeable. The outer ring of material 419 is preferably a fluid impermeable material such as molded closed cell foam. Alternatively, the inner and outer rings of material 417 and 419 may both be fluid absorbent, yet exhibit different degrees of absorbency. For example, the inner ring of material 417 may comprise a very open porous material into which thick, viscous exudate is readily absorbed. In this case, the outer ring of material 219 may comprise a somewhat less open material into which thinner, less viscous exudate is received. The inner and outer rings of material 417 and 419 may be molded separately and bonded together or formed in a multi-step molding process. The cover 412 may comprise a thin molded sheet of flexible, transparent plastic material that may be bonded by a continuous fluid-impervious seal (for example adhesive) to the sidewall 416 in the manner shown in the figures. The bond that joins the cover 412 with the sidewall 416 may be a permanent bond, or an adhesive seam the permits the cover 412 to be removed from the sidewall 416. For example the cover 415 may comprise a molded 4 mil-thick sheet of polyethylene or equivalent material. Since the inside surface 421 of the sidewall 416 is fluid permeable, it permits exudate from the wound 430 to be absorbed into the fluid-absorbent material of the inner ring of material 417. However, the fluid-impermeable treatment of the second skin-facing surface 418 and the fluid-impermeable material of the outer ring of material 419 prevent fluid which has been absorbed into the inner ring of material 417 from moistening healthy skin underneath or outside of the second skin-facing surface 418. In operation, the ring of adhesive material 428 is prepared for attachment to the skin surface, and the bandage 410 is attached via the ring of adhesive material 428 to the skin surface, positioned so that the inner margin 420 surrounds the wound 430, set back from the peri-wound area 432. As exudate is produced in the bed of the wound 430, it flows across the peri-wound area 432, contacting the molded open cell foam material of the inner ring of material 417 at, near, and above the inner margin 420 along the surface 421, where it is absorbed into the bandage 410. At the same time, fluid evaporates from the wound 430 and the skin, increasing the relative humidity within the enclosure formed by the cover 412 and the sidewall 416 to near 100%. This prevents the wound 430 from drying out. Preferably, the MVTR through the bandage 410 is slight compared to the amount of fluid exuded from the wound 430. The grooves 425 provide channels that promote the flow of fluid exuded from the wound 430 along the upper surface of the sidewall 416. Thus, if the bandage 410 is disposed so as to not to be absolutely horizontal, fluid from the wound 430 may flow along one or more of the grooves 425 to be absorbed into the material of the inner ring of material 417.

Figure 5:
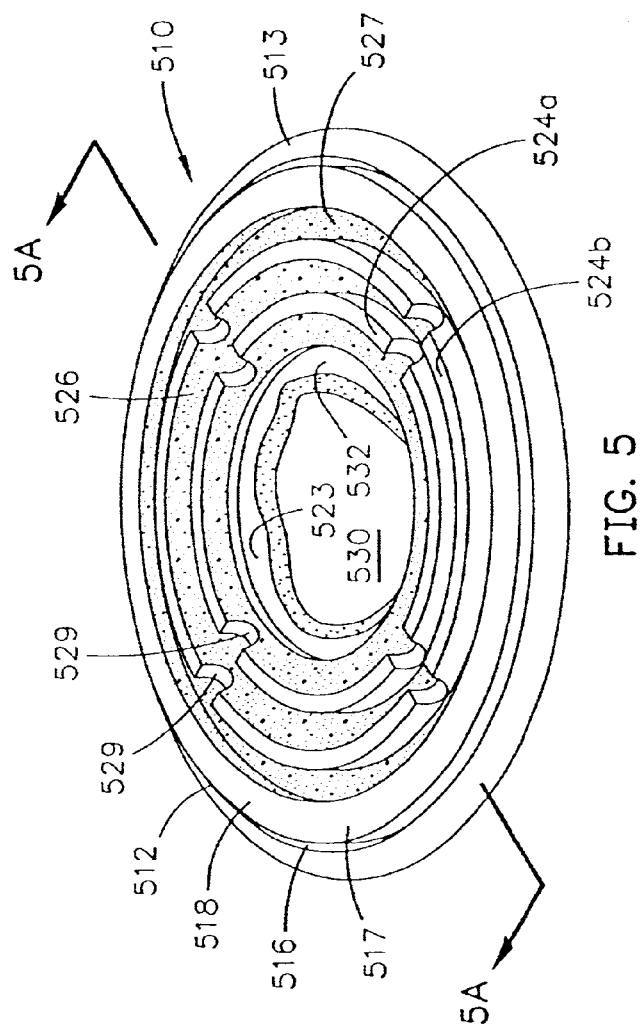
FIG. 5 is an isometric drawing of a fifth embodiment of a bandage for autolytic debridement.
Figure 5A:
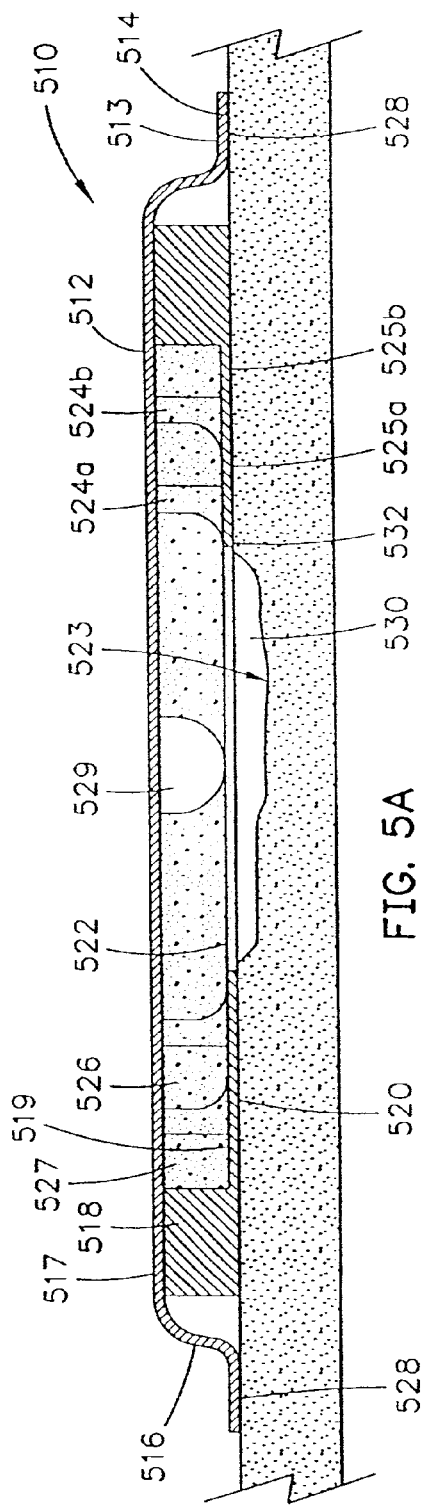
FIG. 5A is a side sectional view taken along A—A of FIG. 5.

FIGS. 5 and 5A illustrate a fifth embodiment of a bandage for autolytic debridement according to our invention. The bandage 510 includes a cover 512 identical to the cover 412 of the fourth embodiment illustrated in FIGS. 4 and 4A. In this regard the cover 512 is a molded. circularly-shaped piece that has a lip 513 and first skin-facing surface 514. The sidewall 516 of the fifth embodiment bandage includes a flat circular container 517 having a circumferential outer rim 518 that rises above a floor 519. A second skin-facing surface 520 is on the bottom of the flat circular container 517. An inner margin 522 defines an opening 523 through the floor 519 of the flat circular container 517. Concentric rings of material 524a and 524b are disposed within the flat circular container 517. The diameter of the first ring of material 594a is less than the diameter of the second ring of material 524b; both rings of material are substantially centered in and concentric with the outer rim 518 of the flat circular container 517. Preferably, the elements of the sidewall 516, including the flat circular container 517, the first ring of material 524a, and second ring of material 524b, are all fluid absorbent, preferably made of a molded open cell foam material. However, at least the second skin-facing surface 520 of the flat circular container 517 is treated as described above with reference to the first embodiment so as to be fluid impermeable. All surfaces of the first and second rings of material 524a and 524b and the interior surface of the flat circular container 517 are not treated and are therefore fluid permeable, enabling the flow of exudate through those surfaces into the material of which their respective structures are formed. Preferably, the flat circular container 517, the first ring of material 524a and the second ring of material 524b are an integral piece, either formed in the same or successive steps, or formed separately and bonded together. Concentric channels 526 and 527 are formed between the first ring of material 524a and the second ring of material 524b, and between the second ring of material 524b and the outer rim 518 of the flat circular container. In addition, radial channels are formed by notches 529 formed in the first and second rings of material 524a and 524b that are aligned along a radius of the flat circular container 517. A ring of adhesive material 528 is mounted on the first skin-facing surface 514 on the cover 512. The ring of adhesive material 528 may have a release liner on its lower surface which is stripped away when the bandage 510 is to be attached to the skin of the patient. As the figures show, the bandage 510 is attached to the skin of a patient by the ring of adhesive material 528 such that the opening 523 defined by the inner margin 522 surrounds the bed of a wound 530 and a ring of peri-wound tissue 532 immediately adjacent the wound 530. Above the opening 523, the space defined between the cover 512 and the sidewall 516 forms a closed structure over the wound 530 which spans the wound 530 without contacting it. The cover 512 and sidewall 516 are separate, single pieces. Preferably the sidewall 516 is formed as described above, comprising a material that is light, flexible, yet of a nature that provides structural integrity to the bandage 510 and support to the cover 512, allowing the bandage 510 to stand up right when attached as shown in the figures. The cover 512 may comprise the material of, and be formed as described above in connection with, the fourth embodiment. The cover 512 may be bonded by a continuous fluid-impervious seal to the sidewall 516 in the manner shown in the figures. The bond that joins the cover 512 with the sidewall 516 may be a permanent bond, or an adhesive seam that permits the cover 512 to be removed from the sidewall 516. Since the inside surfaces of the flat circular container 517 and all surfaces of the first and second rings 524a and 524b are fluid permeable, exudate from the wound 530 is permitted to be absorbed into the fluid absorbent material of which the flat circular container 517 and the rings 524a and 524b are formed. However, the fluid-impermeable treatment of the second skin-facing surface 520 makes that surface fluid-impermeable, thereby preventing fluid which has been absorbed into the sidewall 516 from moistening healthy skin underneath the skin-facing surface 520. In operation, the ring of adhesive material 528 is prepared for attachment to the skin surface, and the bandage 510 is attached via the ring of adhesive material 528 to the skin surface, positioned so that the inner margin 520 surrounds the wound 530, set back from the peri-wound area 532. As exudate is produced in the bed of the wound 530, it flows across the peri-wound area 532, contacting the fluid absorbent material of the first and second rings of material 524a and 524b. In addition, the radial channels formed by the notches 529 provide ingress to the exudate fluid into the concentric channels 526 and 527. The concentric channels 526 and 527 conduct and distribute the fluid over the sidewalls of the rings of material 524a and 524b, the floor 519 of the flat circular container 517 and the inner wall of the outer rim 518. All of these surfaces are fluid permeable and provide a path into the fluid absorbent material of which their respective structures are formed. Reference is made to a first circular tear line 525a in the channel 526 between the first and second rings of material 524a and 524b and a second tear line 525b in the channel 527 between the second ring of material 524b and the outer rim 518. These lines of weakness permit the flat circular container 517 to be modified by removal of annular sections of the sidewall 516. For example, the portion of the sidewall between the first tear line 525a and the inner margin 522 may be separated entirely from and removed from the bandage 510. This provides an opening 523 having a larger diameter then that shown in FIG. 5 and moves the inner margin 522 diametrically toward the outer rim 518. These tear lines permit the bandage 510 to be configured to accommodate wounds of varying sizes.

Figure 6:
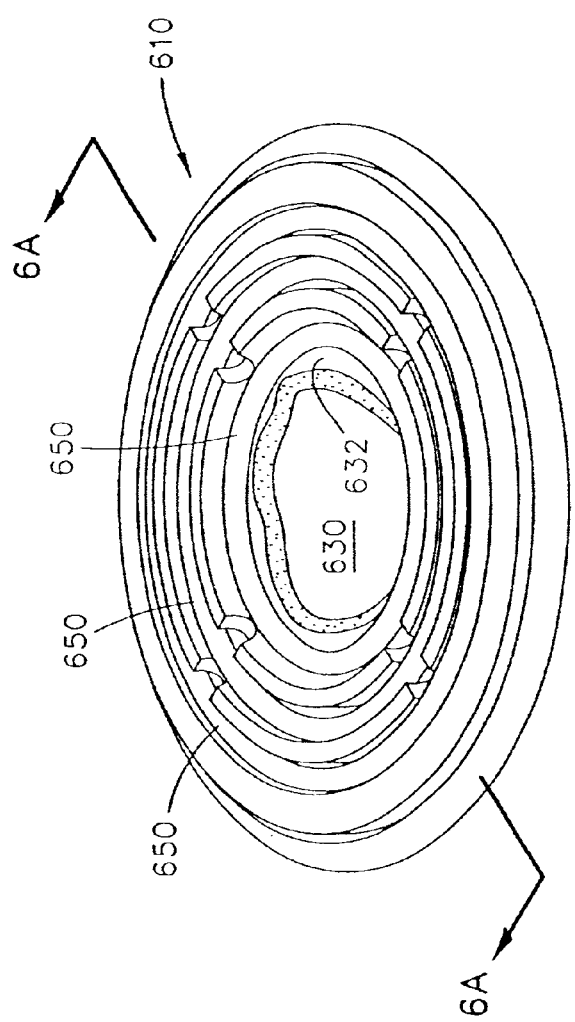
FIG. 6 is an isometric drawing of a sixth embodiment of a bandage for autolytic debridement.
Figure 6A:
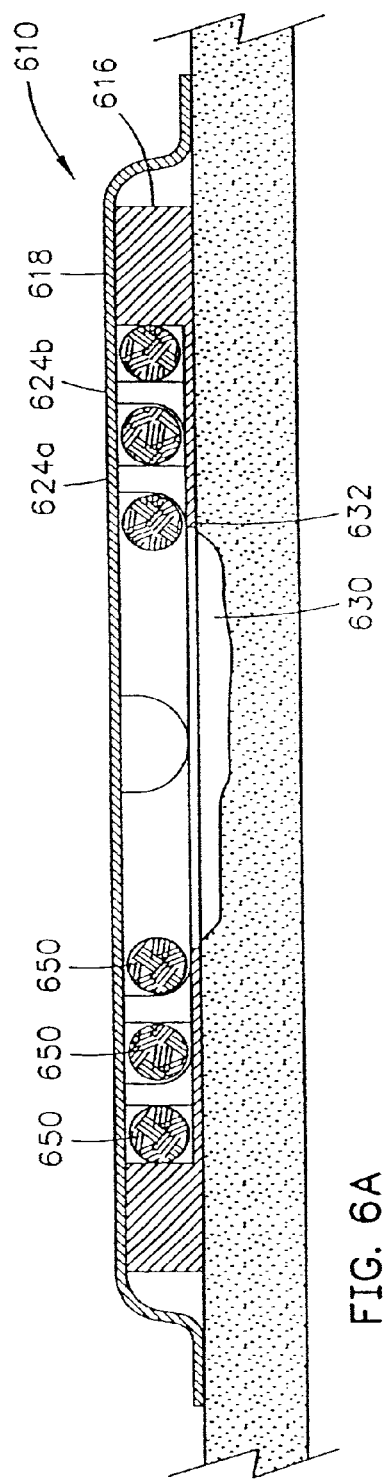
FIG. 6A is a side sectional view taken along A—A of FIG. 6.

FIGS. 6 and 6A illustrate a sixth embodiment of a bandage for autolytic debridement according to our invention. The bandage 610 is identical in all respects with the bandage 510 illustrated in FIGS. 5 and 5A. In addition, circular members 650 are disposed within the sidewall 616, concentrically interspersed with the first ring of material 624a, the second ring of material 624b, and the outer rim 618 of the sidewall 616. Each of the circular members 650 comprises a fluid absorbent material such as an alginate, hydrogel, or hydrocolloid. Alternatively, the circular members 650 can comprise a wicking material. In either case (or in both cases if both types of materials are used), the circular members 650 promote the transport and absorption of exudate fluid from the wound 630 and the pen-wound area 632 to and into the fluid absorbing members of the sidewall 618.

Figure 7:
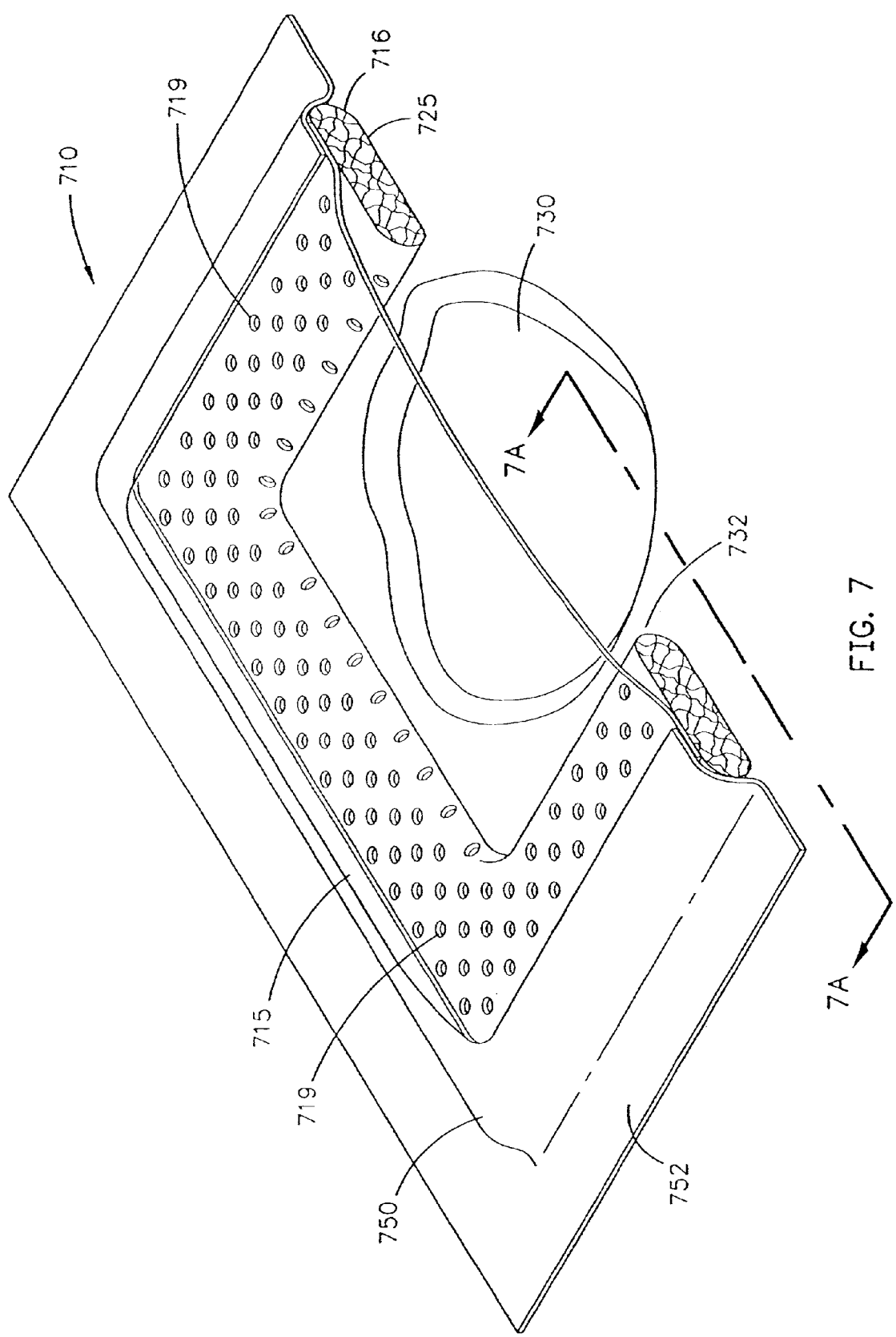
FIG. 7 is an isometric section illustrating a seventh embodiment of a bandage for autolytic debridement.
Figure 7A:
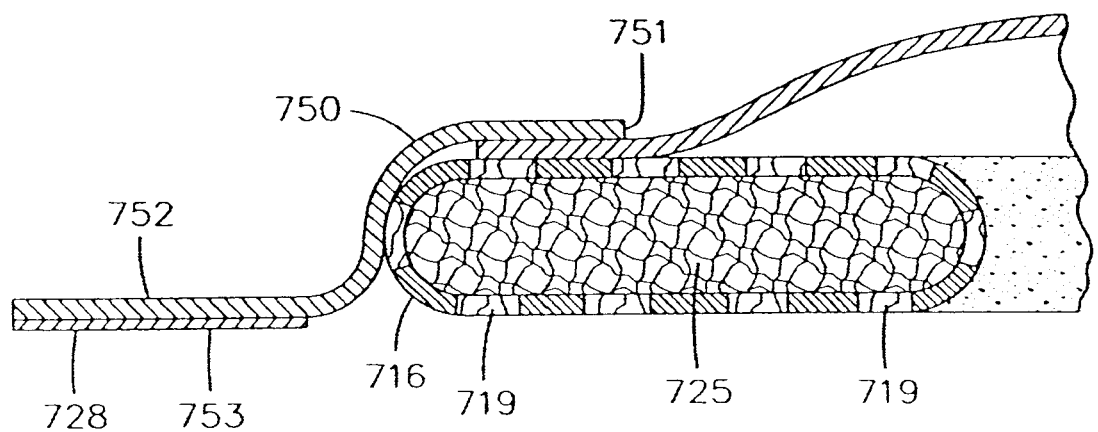
FIG. 7A is a side sectional view taken along A—A of FIG. 7.

FIGS. 7 and 7A illustrate a seventh embodiment of a bandage for autolytic debridement according to our invention. The bandage 710 includes a sidewall 716 that is identical in all respects with the sidewall 316 of the third embodiment illustrated in FIGS. 3 and 3A, with one exception. That exception is that the entire surface of the sidewall 716 is apertured by holes 719 that permit exudate to enter the sidewall the 716, there to be absorbed by fluid-absorbent material 725. A cover 715 identical in all respects with the cover 315 of the third embodiment bandage 310 is sealingly bonded to the sidewall 716. An additional shaped or molded plastic member 750 in the shape of a square or rectangular annulus or skirt is bonded near a first edge 751 to an upper surface of the cover 715 along the periphery of the cover 715 by a continuous, fluid-impervious seal. The plastic member 750 is shaped to transition to a lip 752, a bottom surface of which forms a skin-facing surface 753 on which is mounted a ring of adhesive material 728. The structure, materials and operation of the bandage 710 are as described above for the bandage 310. Preferably, the plastic member 750 is more flexible than the cover 715, not needing the dome-supporting ability of that element.

Manifestly, each of the seven embodiments illustrated in the figures and discussed in the specification forms a sealed enclosure that satisfies the three purposes set forth above for the first embodiment. That is, each embodiment absorbs exudate produced at a wound, retaining most of if not all of the exudate in fluid-absorbent material that is brought into the structure of the bandage at least on an inside surface that is near a margin defining an opening about a wound. This eliminates pooling of exudate in the wound and promotes autolytic debridement. This structure also prevents contamination and the spread of pathogens and odors. Second, each embodiment of the bandage maintains an environment of high relative humidity over a wound. Finally, each embodiment provides a sealed enclosure which, together with the humid atmosphere within the enclosure, effectively thermally insulates a wound and peri-wound area from an ambient environment, which tends to maintain the temperature of the wound and peri-wound area in a normothermic range of from about 36° C. to about 38° C.

In the description of our invention, we have disclosed certain structural members of a bandage for autolytic debridement as comprising fluid-absorbent material. One specific instantiation of such material has been disclosed: molded open-cell foam. This is not intended to limit the practice of our invention to the use of that specific material. Instead, any material that can provide the necessary structural features is contemplated, so long as one or more surfaces of a member made of the material can be made fluid-impermeable without limitation. Other fluid absorbent materials may include hydrogels and hydrocolloids, for example.

Other features may be incorporated into our invention. For example, in any of the embodiments shown, the fluid absorbing material may be impregnated with hydrophilic material to increase its fluid-storing capacity, with odor-absorbing material, such as charcoal, and/or with treatment material such as antibiotics or medicants.

Moreover, features, functions and/or structures described for one embodiment may be incorporated into one or more of the other embodiments. For example, the ability to detach rings in the fifth and sixth embodiments may be incorporated in the fourth. Variability in the fluid absorption characteristics of different members that was described in connection with the fourth embodiment could be incorporated into at least the fifth and sixth, if not all of the remaining embodiments.

This description may have described features, elements, and limitations of our invention in the singular. This is not meant to so limit the implementation of our invention in any case where the plural could be used.

It should be clear that our invention comprehends a method for treating a wound by promoting autolytic debridement. In this regard, a wound treatment apparatus (or "bandage" or "plaster") having a fluid impermeable enclosure with a sidewall forming a margin that defines an opening is provided, the wound treatment apparatus including a fluid absorbent material disposed in the enclosure. The fluid absorbent material is disposed at, or near the margin, out of the opening. The wound treatment device also includes an attachment device (or a means for attachment) on a skin-facing surface of the enclosure. The enclosure is brought against the surface of a human (or animal) body such that the attachment device attaches the wound treatment device to the surface at a location that creates a closed, substantially fluid impermeable environment over a wound, with the wound in the opening, substantially encircled by the margin. The closed, substantially, fluid impermeable environment creates a humid atmosphere within the enclosure, about the wound that maintains a temperature about the wound at or near a normothermic level in the range of about 36° C. to about 38° C. Fluid exudate produced in or near the wound is collected and held in the fluid absorbent material as the wound heals.

While our invention has been illustrated and described with reference to particular embodiments, it will be understood by those skilled in the art that various changes and modifications can be made to those embodiments, and other embodiments can be provided, without departing from the scope of the invention, which is limited only by the following claims.

We claim:

1. A bandage for autolytic debridement, comprising:
    an enclosure having a fluid-impermeable outer surface, a sidewall that forms a margin defining an opening, and a skin-facing surface surrounding the opening;
    an attachment means disposed on the skin-facing surface for attaching the enclosure to skin with the margin surrounding a wound such that the enclosure creates a closed, fluid-impermeable chamber over the wound, substantially without contacting the wound; and
    a fluid absorbent material disposed within the enclosure substantially near the margin and out of the opening;
    the enclosure being formed of the fluid absorbent material;
    the fluid absorbent material being selected from the group consisting of hydrogels and hydrocolloids.

2. A bandage for autolytic debridement, comprising:
    an enclosure having a fluid-impermeable outer surface, a sidewall that forms a margin defining an opening, and a skin-facing surface surrounding the opening;
    an attachment means disposed on the skin-facing surface for attaching the enclosure to skin with the margin surrounding a wound such that the enclosure creates a closed, fluid-impermeable chamber over the wound, substantially without contacting the wound; and
    a fluid absorbent material disposed within the enclosure substantially near the margin and out of the opening;
    the enclosure being formed of the fluid absorbent material;
    the fluid absorbent material being impregnated with a hydrophilic material.

3. A bandage for autolytic debridement, comprising:
    an enclosure having a fluid-impermeable outer surface, a sidewall that forms a margin defining an opening, and a skin-facing surface surrounding the opening;
    an attachment means disposed on the skin-facing surface for attaching the enclosure to skin with the margin surrounding a wound such that the enclosure creates a closed, fluid-impermeable chamber over the wound, substantially without contacting the wound; and
    a fluid absorbent material disposed within the enclosure substantially near the margin and out of the opening;
    the enclosure being formed of the fluid absorbent material;
    the fluid absorbent material being impregnated with an odor absorbing material.

4. The bandage of claims 3, the odor absorbing material including charcoal.

5. A bandage for autolytic debridement, comprising:
    an enclosure having a fluid-impermeable outer surface, a sidewall that forms a margin defining an opening, and a skin-facing surface surrounding the opening;
    an attachment means disposed on the skin-facing surface for attaching the enclosure to skin with the margin surrounding a wound such that the enclosure creates a closed, fluid-impermeable chamber over the wound, substantially without contacting the wound; and
    a fluid absorbent material disposed within the enclosure substantially near the margin and out of the opening;
    the enclosure being formed of the fluid absorbent material;
    the fluid absorbent material being impregnated with a treatment material.

6. The bandage of claim 5, the treatment material including an antibiotic.

7. The bandage of claim 5, the treatment material including a medicament.

8. A bandage for autolytic debridement, comprising:
    an enclosure having a fluid-impermeable outer surface, a sidewall that forms a margin defining an opening, and a skin-facing surface surrounding the opening;
    an attachment means disposed on the skin-facing surface for attaching the enclosure to skin with the margin surrounding a wound such that the enclosure creates a closed, fluid-impermeable chamber over the wound, substantially without contacting the wound; and
    a fluid absorbent material disposed within the enclosure substantially near the margin and out of the opening;
    the sidewall being formed of the fluid absorbent material;
    the fluid absorbent material being selected from the group consisting of hydrogels and hydrocolloids.

9. A bandage for autolytic debridement, comprising:
    an enclosure having a fluid-impermeable outer surface, a sidewall that forms a margin defining an opening, and a skin-facing surface surrounding the opening;
    an attachment means disposed on the skin-facing surface for attaching the enclosure to skin with the margin surrounding a wound such that the enclosure creates a closed, fluid-impermeable chamber over the wound, substantially without contacting the wound; and
    a fluid absorbent material disposed within the enclosure substantially near the margin and out of the opening;
    the sidewall being formed of the fluid absorbent material;
    the fluid absorbent material being impregnated with a hydrophilic material.

10. A bandage for autolytic debridement, comprising:
    an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

the sidewall being formed of the fluid absorbent material;

the fluid absorbing material being impregnated with an odor absorbing material.

11. The bandage of claim 10, the odor absorbing material including charcoal.

12. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

the sidewall being formed of the fluid absorbent material;

the fluid absorbing material being impregnated with a treatment material.

13. The bandage of claim 12, the treatment material including an antibiotic.

14. The bandage of claim 12, the treatment material including a medicament.

15. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound, such that the enclosure creates a closed, fluid-impermeable chamber over the wound, substantially without contacting the wound; and a fluid absorbent material disposed within the enclosure substantially near the margin and out of the opening; and wicking material in contact with the fluid absorbent material;

the fluid absorbent material being selected from the group consisting of hydrogels and hydrocolloids.

16. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening; and wicking material in contact with the fluid absorbent material;

the fluid absorbent material being impregnated with a hydrophillic material.

17. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening; and wicking material in contact with the fluid absorbent material;

the fluid absorbent material being impregnated with an odor absorbing material.

18. The bandage of claim 17, the odor absorbing material including charcoal.

19. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening; and wicking material in contact with the fluid absorbent material;

the fluid absorbent material being impregnated with a treatment material.

20. The bandage of claim 19, the treatment material including an antibiotic.

21. The bandage of claim 19, the treatment material including a medicament.

22. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

wherein the sidewall, forms a pouch containing the fluid absorbent material, the bandage further including apertures in the pouch;

the fluid absorbent material being selected from the group consisting of hyrdogels and hydrocolloids.

23. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

wherein the sidewall forms a pouch containing the fluid absorbent material, the bandage further including apertures in the pouch;

the fluid absorbent material being impregnated with a hydrophilic material.

24. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

wherein the sidewall forms a pouch containing the fluid absorbent material, the bandage further including apertures in the pouch;

the fluid absorbing material being impregnated with an odor absorbing material.

25. The bandage of claim 24, the odor absorbing material including charcoal.

26. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

wherein the sidewall forms a pouch containing the fluid absorbent material, the bandage further including apertures in the pouch;

the fluid absorbent material being impregnated with a treatment material.

27. The bandage of claim 26, the treatment material including an antibiotic.

28. The bandage of claim 26, the treatment material including a medicament.

29. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound;

a fluid absorbent material disposed within the enclosure substantially near the margin and out of the opening;

wicking material; and means acting between the sidewall and the wicking material for supporting the wicking material;

the fluid absorbent material being selected from the group consisting of hydrogels and hydrocolloids.

30. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound;

a fluid absorbent material disposed within the enclosure substantially near the margin and out of the opening;

wicking material; and means acting between the sidewall and the wicking material for supporting the wicking material;

the fluid absorbent material being impregnated with a hydrophilic material.

31. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound;

a fluid absorbent material disposed within the enclosure substantially near the margin and out of the opening;

wicking material; and means acting between the sidewall and the wicking material for supporting the wicking material;

the fluid absorbent material being impregnated with an odor absorbing material.

32. The bandage of claim 31, the odor absorbing material including charcoal.

33. A bandage for autolytic debridement, comprising:

an enclosure having a fluid-impermeable outer surface, a sidewall that forms a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound;

a fluid absorbent material disposed within the enclosure substantially near the margin and out of the opening;

wicking material; and means acting between the sidewall and the wicking material for supporting the wicking material;

the fluid absorbent material being impregnated with a treatment material.

34. The bandage of claim 33, the treatment material including an antibiotic.

35. The bandage of claim 33, the treatment material including a medicament.

36. A bandage for autolytic debridement, comprising:

a fluid impermeable enclosure having a sidewall that forms a margin defining an opening, and a skin-facing surface surrounding the opening;

an adhesive disposed on the skin-facing surface for attaching the enclosure to skin such that the enclosure creates a closed, fluid-impermeable chamber over a wound, out of contact with the wound; and a fluid absorbent material disposed within the enclosure near the margin and out of the opening, the fluid absorbent material having an inside surface and a contoured lip proximate the skin-facing surface, the contoured lip projecting inwardly toward the opening and being configured to promote the flow of fluid upward along the inside surface;

the fluid absorbent material being selected from the group including hyrdogels and hydrocolloids.

37. A bandage for autolytic debridement, comprising:

a fluid impermeable enclosure having a sidewall that forms a margin defining an opening, and a skin-facing surface surrounding the opening;

an adhesive disposed on the skin-facing surface for attaching the enclosure to skin such that the enclosure creates a closed, fluid-impermeable chamber over a wound, out of contact with the wound; and a fluid absorbent material disposed within the enclosure near the margin and out of the opening, the fluid absorbent material having an inside surface and a contoured lip proximate the skin-facing surface, the contoured lip projecting inwardly toward the opening and being configured to promote the flow of fluid upward along the inside surface;

the fluid absorbent material being impregnated with a hydrophilic material.

38. A bandage for autolytic debridement, comprising:

a fluid impermeable enclosure having a sidewall that forms a margin defining an opening, and a skin-facing surface surrounding the opening;

an adhesive disposed on the skin-facing surface for attaching the enclosure to skin such that the enclosure creates a closed, fluid-impermeable chamber over a wound, out of contact with the wound; and a fluid absorbent material disposed within the enclosure near the margin and out of the opening, the fluid absorbent material having an inside surface and a contoured lip proximate the skin-facing surface, the contoured lip projecting inwardly toward the opening and being configured to promote the flow of fluid upward along the inside surface;

the fluid absorbent material being impregnated with an odor absorbing material.

39. The bandage of claim 38, the odor absorbing material including charcoal.

40. A bandage for autolytic debridement, comprising:

a fluid impermeable enclosure having a sidewall that forms a margin defining an opening, and a skin-facing surface surrounding the opening;

an adhesive disposed on the skin-facing surface for attaching the enclosure to skin such that the enclosure creates a closed, fluid-impermeable chamber over a wound, out of contact with the wound; and a fluid absorbent material disposed within the enclosure near the margin and out of the opening, the fluid absorbent material having an inside surface and a contoured lip proximate the skin-facing surface, the contoured lip projecting inwardly toward the opening and being configured to promote the flow of fluid upward along the inside surface;

the fluid absorbent material being impregnated with a treatment material.

41. The bandage of claim 40, the treatment material including an antibiotic.

42. The bandage of claim 40, the treatment material including a medicament.

43. A bandage for autolytic debridement, comprising:

an enclosure having a fluid-impermeable outer surface, a sidewall including at least two members, the sidewall forming a, margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

the fluid absorbent material being selected from the group consisting of hydrogels and hydrocolloids.

44. The bandage of claim 43, wherein the at least two members include two concentric members.

45. The bandage of claim 43, wherein a first member includes the fluid absorbent material and a second member includes a non-fluid absorbent material.

46. The bandage of claim 43, wherein a first member includes a first fluid absorbent material and a second member includes a second fluid absorbent material.

47. A bandage for autolytic debridement, comprising:

an enclosure having a fluid-impermeable outer surface, a sidewall including at least two members, the sidewall forming a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

the fluid absorbent material being impregnated with a hydrophilic material.

48. The bandage of claim 47, Wherein the at least two members include at least two concentric members.

49. The bandage of claim 47, wherein a first member includes the fluid absorbent material and a second member includes a non-fluid absorbent material.

50. The bandage of claim 47, wherein a first member includes a first fluid absorbent material.

51. A bandage for autolytic debridement, comprising:

an enclosure having a fluid-impermeable outer surface, a sidewall including at least two members, the sidewall forming a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

the fluid absorbent material being impregnated with an odor absorbing material.

52. The bandage of claim 51, wherein at least two members include at least two concentric members.

53. The bandage of claim 51, wherein a first member includes the fluid absorbent material and a second member includes a non-fluid absorbent material.

54. The bandage of claim 51, wherein a first member includes a first fluid absorbent material and a second member includes a second fluid absorbent material.

55. The bandage of claim 51, the odor absorbing material including charcoal.

56. The bandage of claim 55, wherein the at least two members include two concentric members.

57. The bandage of claim 55, wherein a first member includes the fluid absorbent material and a second member includes a non-fluid absorbent material.

58. The bandage of claim 55, wherein a first member includes a fluid absorbent material and a second member includes a second fluid absorbent material.

59. A bandage for autolytic debridement, comprising:

an enclosure having a fluid-impermeable outer surface, a sidewall including at least two members, the sidewall forming a margin defining an opening, and a skin-facing surface surrounding the opening;

an attachment means disposed on the skin-facing surface for attaching the enclosure to skin with the margin surrounding a wound such that the enclosure creates a closed, fluid-impermeable chamber over the wound, substantially without contacting the wound; and a fluid absorbent material disposed within the enclosure substantially near the margin and out of the opening;

the fluid absorbing material being impregnated with a treatment material.

60. The bandage of claim 59, wherein the at least two members include two concentric members.

61. The bandage of claim 59, wherein a first member includes the fluid absorbent material and a second member includes a non-fluid absorbent material.

62. The bandage of claim 59, wherein a first member includes a fluid absorbent material and a second member includes a second fluid absorbent material.

63. The bandage of claim 62, the treatment material including an antibiotic.

64. The bandage of claim 63, wherein the at least two members include two concentric members.

65. The bandage of claim 63, wherein a first member includes the fluid absorbent material and a second member includes a non-fluid absorbent material.

66. The bandage of claim 63, wherein a first member includes a fluid absorbent material and a second member includes a second fluid absorbent material.

67. The bandage of claim 59, the treatment material including a medicament.

68. The bandage of claim 67, wherein the at least two members include two concentric members.

69. The bandage of claim 67, wherein a first member includes the fluid absorbent material and a second member includes a non-fluid absorbent material.

70. The bandage of claim 67, wherein a first member includes a fluid absorbent material and a second member includes a second fluid absorbent material.

* * * * *